(12) United States Patent
Brown

(10) Patent No.: US 7,912,688 B2
(45) Date of Patent: Mar. 22, 2011

(54) DISEASE SIMULATION SYSTEM AND METHOD

(75) Inventor: Stephen J. Brown, Woodside, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 3 days.

(21) Appl. No.: 11/656,168

(22) Filed: Jan. 22, 2007

(65) Prior Publication Data
US 2007/0118348 A1    May 24, 2007

Related U.S. Application Data

(63) Continuation of application No. 09/810,865, filed on Mar. 16, 2001, now Pat. No. 7,167,818, which is a continuation of application No. 09/399,122, filed on Sep. 20, 1999, now Pat. No. 6,233,539, which is a continuation of application No. 08/781,278, filed on Jan. 10, 1997, now Pat. No. 5,956,501.

(51) Int. Cl.
G06G 7/58    (2006.01)
(52) U.S. Cl. .......................................... 703/11
(58) Field of Classification Search ........................ 703/6
See application file for complete search history.

(56) References Cited

U.S. PATENT DOCUMENTS

| | | | |
|---|---|---|---|
| 4,731,726 A | 3/1988 | Allen, III | |
| 5,019,974 A | 5/1991 | Beckers | |
| 5,171,977 A | 12/1992 | Morrison | |
| 5,251,126 A | 10/1993 | Kahn et al. | |
| 5,307,263 A | * 4/1994 | Brown ........................ | 600/301 |
| 5,321,009 A | 6/1994 | Baeder et al. | |
| 5,325,288 A | 6/1994 | Satou | |
| 5,343,387 A | 8/1994 | Honma et al. | |

(Continued)

FOREIGN PATENT DOCUMENTS
EP    0558975    9/1993

(Continued)

OTHER PUBLICATIONS

Lehmann et al.; Computer assisted diabetes care: a 6 year retrospective; computer methods and programs in biomedicine; 1996; pp. 209-230.*

(Continued)

*Primary Examiner* — Hugh Jones
(74) *Attorney, Agent, or Firm* — Christopher P. Maiorana, PC

(57) ABSTRACT

A system and method for predicting the effect of patient self-care actions on a disease control parameter. A future disease control parameter value $X(t_j)$ at time $t_j$ is determined from a prior disease control parameter value $X(t_i)$ at time $t_i$ based on an optimal control parameter value $R(t_j)$ at time $t_j$, the difference between the prior disease control parameter value $X(t_i)$ and an optimal control parameter value $R(t_i)$ at time $t_i$, and a set of differentials between patient self-care parameters having patient self-care values $S_M(t_i)$ at time $t_i$ and optimal self-care parameters having optimal self-care values $O_M(t_i)$ at time $t_i$. The differentials are multiplied by corresponding scaling factors $K_M$. The system includes an input device for entering the patient self-care values $S_M(t_i)$. A memory stores the optimal control parameter values $R(t_i)$ and $R(t_j)$, the prior disease control parameter value $X(t_i)$, the optimal self-care values $O_M(t_i)$, and the scaling factors $K_M$. A processor in communication with the input device and memory calculates the future disease control parameter value $X(t_j)$. A display is connected to the processor to display the future disease control parameter value $X(t_j)$ to a patient.

19 Claims, 8 Drawing Sheets

U.S. PATENT DOCUMENTS

| | | | |
|---|---|---|---|
| 5,394,322 | A | 2/1995 | Hansen |
| 5,431,690 | A | 7/1995 | Schaldach et al. |
| 5,438,983 | A | 8/1995 | Falcone |
| 5,454,721 | A | 10/1995 | Kuch |
| 5,471,382 | A | 11/1995 | Tallman et al. |
| 5,519,058 | A | 5/1996 | Gonick et al. |
| 5,523,232 | A | 6/1996 | Sechler |
| 5,572,646 | A | 11/1996 | Kawai et al. |
| 5,635,532 | A | 6/1997 | Samid |
| 5,642,731 | A | 7/1997 | Kehr |
| 5,651,363 | A | 7/1997 | Kaufman et al. |
| 5,659,691 | A | 8/1997 | Durward et al. |
| 5,680,866 | A | 10/1997 | Kangas et al. |
| 5,710,178 | A | 1/1998 | Samid |
| 5,730,124 | A | 3/1998 | Yamauchi |
| 5,730,654 | A | 3/1998 | Brown |
| 5,754,740 | A | 5/1998 | Fukuoka et al. |
| 5,758,652 | A | 6/1998 | Nikolic |
| 5,822,715 | A | 10/1998 | Worthington et al. |
| 5,840,020 | A | 11/1998 | Heinonen et al. |
| 5,956,501 | A | 9/1999 | Brown |
| 5,966,526 | A | 10/1999 | Yokoi |
| 5,971,855 | A | 10/1999 | Ng |
| 5,971,922 | A | 10/1999 | Arita et al. |
| 5,983,003 | A | 11/1999 | Lection et al. |
| 6,102,855 | A | 8/2000 | Kehr et al. |
| 6,186,145 | B1 | 2/2001 | Brown |
| 6,233,539 | B1 | 5/2001 | Brown |
| 6,246,975 | B1 | 6/2001 | Rivonelli et al. |
| 6,494,830 | B1 | 12/2002 | Wessel |

FOREIGN PATENT DOCUMENTS

| | | |
|---|---|---|
| EP | 08131551 | 12/1997 |
| WO | WO-9636923 | 11/1996 |

OTHER PUBLICATIONS

Lehmann et al.; Computer assisted diabetes care: a 6 year retrospective; Computer Methods and Programs in Biomedicine 50 (1996) 209-230.*

Carson et al.; A Spectrum of Approaches for Controlling Diabetes; 0272-1708/92/$03.000 1992IEEE; 1992; pp. 25-31.*

Fischer et al; Knowledge-based Education Tool to Improve Quality in Diabetes Care; vol. 934/1995; pp. 417-418; Lecture Notes in Computer Science; Springer Berlin / Heidelberg.*

Bellazzi et al.; Adaptive controllers for intelligent monitoring; Artificial Intelligence in Medicine 7 (1995) 515-540.*

Ambrosiadoua et al; Clinical evaluation of the Diabetes expert system for decision support by multiple regim.en insulin dose adjustment; Computer Methods and Programs in Biomedicin4e9 (1996)105-115.*

Lehmann et al.; An interactive, educational model for insulin dosage and dietary adjustment in type I diabetes mellitus; pp. 205-209; 0195-4210/92/$5.00 0 1993 AMIA, Inc.*

Cavan et al.; Use of the DIAS model to predict unrecognised hypoglycaemia in patients with insulin-dependent diabetes; Computer Methodsa ndP rogramisn Biomedicin5e0 ( 1996)2 41-246.*

Zviran et al.; DMSSnA Computer-Based Diabetes Monitoring System; Journal of Medical Systems, vol. 13, No. 5, 1989.*

* cited by examiner

PHYSIOLOGICAL PARAMETERS ENTRY SCREEN

BODY MASS (KG): 78 ~43
METABOLISM RATE: HIGH
FITNESS LEVEL: LOW

OK ~45

CANCEL ~47

INSULIN SENSITIVITIES:
HEPATIC (SH) 0.4
PERIPHERAL (SP) 0.6

*FIG. 2*

SELF-CARE PARAMETERS ENTRY SCREEN

| FOOD EXCHANGES: | BREAKFAST | LUNCH | DINNER |
|---|---|---|---|
| TIME (HH:MM) | 08:00 | 12:00 | 18:00 ~51 |
| CARBOHYDRATE (G) | 40 | 40 | 30 ~53 |

| INSULIN INJECTIONS: | DOSE 1 | DOSE 2 | DOSE 3 |
|---|---|---|---|
| TIME (HH:MM) | 08:00 | 12:00 | 18:00 |
| DOSE (UNITS) | 15 | 10 | 12 |

| EXERCISE: | SESSION 1 | SESSION 2 | SESSION 3 |
|---|---|---|---|
| TIME (HH:MM) | 15:00 | | |
| DURATION (15 MIN. UNITS) | 2 | | |

55~ OK          CANCEL ~57

*FIG. 3*

| t | R(t) | X(t) | $S_1(t) - O_1(t)$ | $S_2(t) - O_2(t)$ | $S_3(t) - O_3(t)$ | $K_1$ | $K_2$ | $K_3$ |
|---|---|---|---|---|---|---|---|---|
| 8:00 | 80 | 80 | 0 | 0 | 0 | 4 | -40 | -5 |
| 10:00 | 160 | 160 | 0 | 0 | 0 | 4 | -40 | -5 |
| 12:00 | 100 | 100 | 0 | 0 | 0 | 4 | -40 | -5 |
| 15:00 | 140 | 140 | 0 | 0 | 0 | 4 | -40 | -5 |
| 18:00 | 100 | 100 | 0 | 0 | 0 | 4 | -40 | -5 |
| 20:00 | 180 | 180 | 0 | 0 | 0 | 4 | -40 | -5 |
| 22:00 | 120 | 120 | 0 | 0 | 0 | 4 | -40 | -5 |

| t | R(t) | X(t) | $S_1(t) - O_1(t)$ | $S_2(t) - O_2(t)$ | $S_3(t) - O_3(t)$ | $K_1$ | $K_2$ | $K_3$ |
|---|---|---|---|---|---|---|---|---|
| 8:00 | 80 | 80 | 10 | 0 | 0 | 4 | -40 | -5 |
| 10:00 | 160 | 200 | 0 | 0 | 0 | 4 | -40 | -5 |
| 12:00 | 100 | 140 | 0 | 0 | 0 | 4 | -40 | -5 |
| 15:00 | 140 | 180 | 0 | 0 | 4 | 4 | -40 | -5 |
| 18:00 | 100 | 120 | 0 | 0 | 0 | 4 | -40 | -5 |
| 20:00 | 180 | 200 | 0 | 0 | 0 | 4 | -40 | -5 |
| 22:00 | 120 | 140 | 0 | 0 | 0 | 4 | -40 | -5 |

| t | $R(t)$ | $X(t)$ | $S_1(t) - O_1(t)$ | $S_2(t) - O_2(t)$ | $S_3(t) - O_3(t)$ | $K_1$ | $K_2$ | $K_3$ |
|---|---|---|---|---|---|---|---|---|
| 8:00 | 80 | 80 | 10 | 0 | 0 | 4 | -40 | -5 |
| 10:00 | 160 | 200 | 0 | 1 | 0 | 4 | -40 | -5 |
| 12:00 | 100 | 100 | 0 | 0 | 0 | 4 | -40 | -5 |
| 15:00 | 140 | 140 | 0 | 0 | 4 | 4 | -40 | -5 |
| 18:00 | 100 | 80 | 5 | 0 | 0 | 4 | -40 | -5 |
| 20:00 | 180 | 180 | 0 | 0 | 0 | 4 | -40 | -5 |
| 22:00 | 120 | 120 | 0 | 0 | 0 | 4 | -40 | -5 |

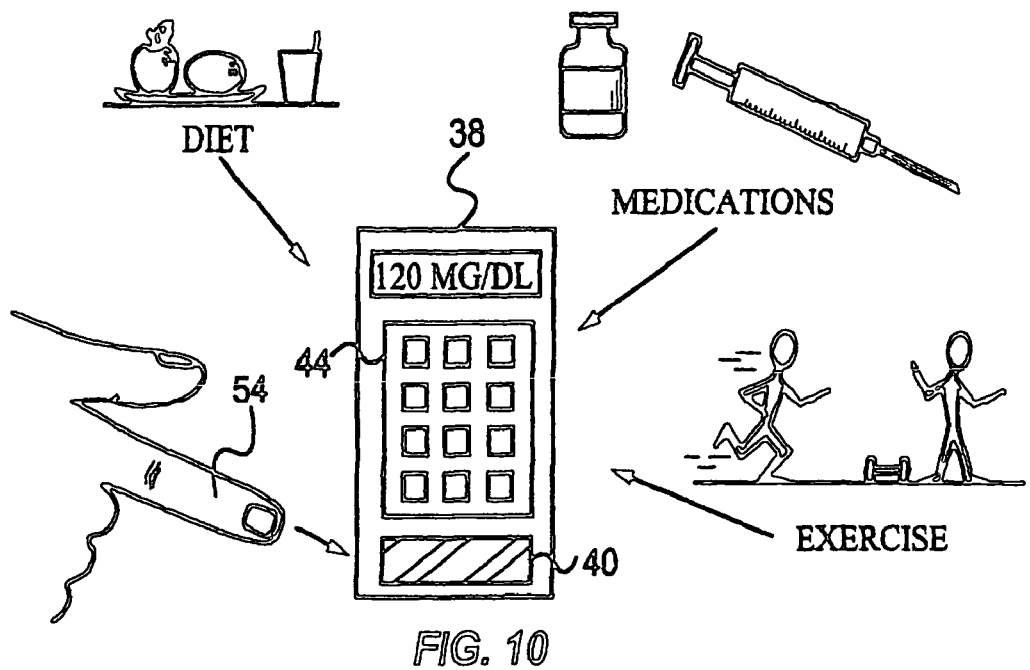
FIG. 10
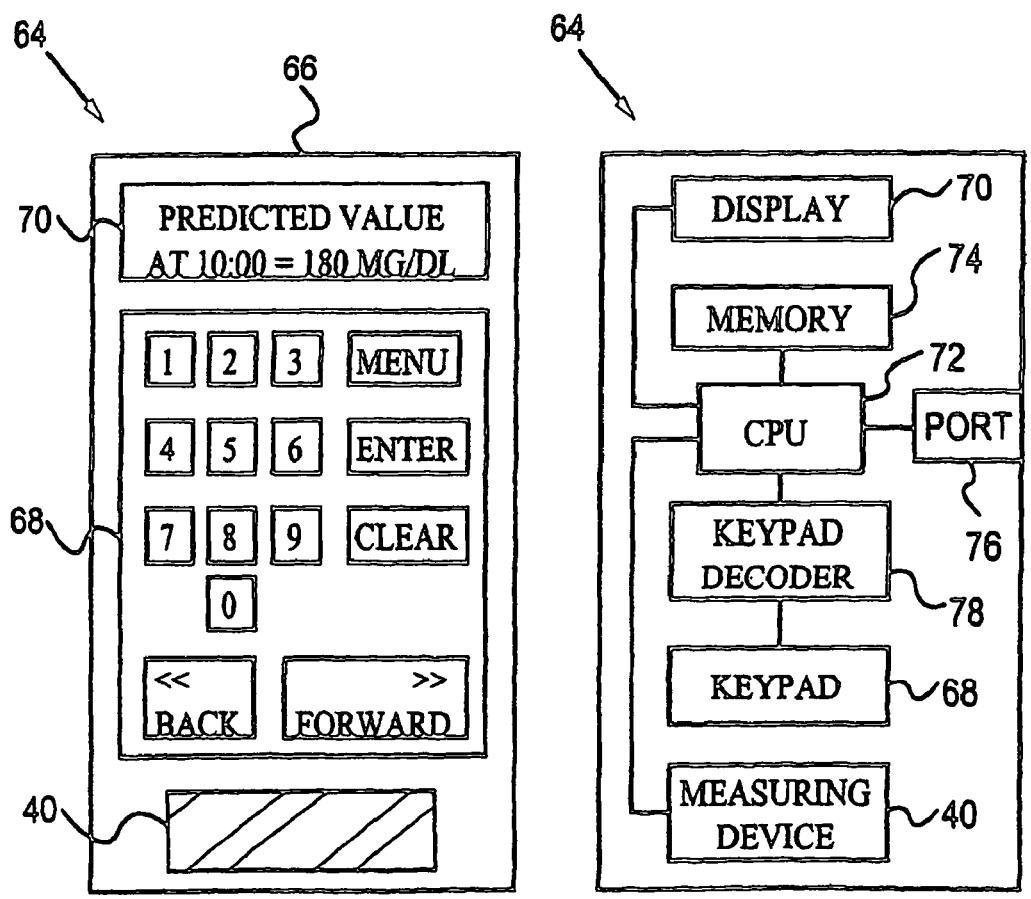
FIG. 11
FIG. 12

DISEASE SIMULATION SYSTEM AND METHOD

CROSS-REFERENCE TO RELATED APPLICATIONS

This application is a continuation of patent application Ser. No. 09/810,865, filed Mar. 16, 2001, now U.S. Pat. No. 7,167,818 which is a continuation of Ser. No. 09/399,122, filed Sep. 20, 1999, now U.S. Pat. No. 6,233,539, which is a continuation of Ser. No. 08/781,278 filed Jan. 10, 1997, now U.S. Pat. No. 5,956,501, each of which are herein incorporated by reference.

BACKGROUND

1. Field of the Invention

The present invention relates generally to disease simulation systems, and in particular to a system and method for simulating a disease control parameter and for predicting the effect of patient self-care actions on the disease control parameter.

2. Description of Prior Art

Managing a chronic disease or ongoing health condition requires the monitoring and controlling of a physical or mental parameter of the disease. Examples of these disease control parameters include blood glucose in diabetes, respiratory flow in asthma, blood pressure in hypertension, cholesterol in cardiovascular disease, weight in eating disorders, T-cell or viral count in HIV, and frequency or timing of episodes in mental health disorders. Because of the continuous nature of these diseases, their corresponding control parameters must be monitored and controlled on a regular basis by the patients themselves outside of a medical clinic.

Typically, the patients monitor and control these parameters in clinician assisted self-care or outpatient treatment programs. In these treatment programs, patients are responsible for performing self-care actions which impact the control parameter. Patients are also responsible for measuring the control parameter to determine the success of the self-care actions and the need for further adjustments. The successful implementation of such a treatment program requires a high degree of motivation, training, and understanding on the part of the patients to select and perform the appropriate self-care actions.

One method of training patients involves demonstrating the effect of various self-care actions on the disease control parameter through computerized simulations. Several computer simulation programs have been developed specifically for diabetes patients. Examples of such simulation programs include BG Pilot™ commercially available from Raya Systems, Inc. of 2570 El Camino Real, Suite 520, Mountain View, Calif. 94040 and AIDA freely available on the World Wide Web at the Diabetes UK website http://www.pcug.co.uk/diabetes/aida.htm.

Both BG Pilot™ and AIDA use mathematical compartmental models of metabolism to attempt to mimic various processes of a patient's physiology. For example, insulin absorption through a patient's fatty tissue into the patient's blood is represented as a flow through several compartments with each compartment having a different flow constant. Food absorption from mouth to stomach and gut is modeled in a similar manner. Each mathematical compartmental model uses partial differential equations and calculus to simulate a physiological process.

This compartmental modeling approach to disease simulation has several disadvantages. First, understanding the compartmental models requires advanced mathematical knowledge of partial differential equations and calculus which is far beyond the comprehension level of a typical patient. Consequently, each model is an unfathomable "black box" to the patient who must nevertheless trust the model and rely upon it to learn critical health issues.

A second disadvantage of the compartmental modeling approach is that a new model is needed for each new disease to be simulated. Many diseases involve physiological processes for which accurate models have not been developed. Consequently, the mathematical modeling approach used in BG Pilot™ and AIDA is not sufficiently general to extend simulations to diseases other than diabetes.

A further disadvantage of the modeling approach used in BG Pilot™ and AIDA is that the mathematical models are not easily customized to an individual patient. As a result, BG Pilot™ and AIDA are limited to simulating the effect of changes in insulin and diet on the blood glucose profile of a typical patient. Neither of these simulation programs may be customized to predict the effect of changes in insulin and diet on the blood glucose profile of an individual patient.

OBJECTS AND ADVANTAGES OF THE INVENTION

In view of the above, it is an object of the present invention to provide a disease simulation system which is sufficiently accurate to teach a patient appropriate self-care actions and sufficiently simple to be understood by the average patient. It is another object of the invention to provide a disease simulation system which may be used to simulate many different types of diseases. A further object of the invention is to provide a disease simulation system which may be easily customized to an individual patient.

These and other objects and advantages will become more apparent after consideration of the ensuing description and the accompanying drawings.

SUMMARY OF THE INVENTION

The invention presents a system and method for simulating a disease control parameter and for predicting the effect of patient self-care actions on the disease control parameter. According to the method, a future disease control parameter value $X(t_j)$ at time $t_j$ is determined from a prior disease control parameter value $X(t_i)$ at time $t_i$ based on an optimal control parameter value $R(t_j)$ at time $t_j$, the difference between the prior disease control parameter value $X(t_i)$ and an optimal control parameter value $R(t_i)$ at time $t_i$, and a set of differentials between patient self-care parameters having patient self-care values $S_M(t_i)$ at time $t_i$ and optimal self-care parameters having optimal self-care values $O_M(t_i)$ at time $t_i$. In the preferred embodiment, the differentials are multiplied by corresponding scaling factors $K_M$ and the future disease control parameter value $X(t_j)$ is calculated according to the equation:

$$X(t_j) = R(t_j) + (X(t_i) - R(t_i)) + \sum_M K_M (S_M(t_i) - O_M(t_i))$$

A preferred system for implementing the method includes an input device for entering the patient self-care values $S_M(t_i)$. The system also includes a memory for storing the optimal control parameter values $R(t_i)$ and $R(t_j)$, the prior disease control parameter value $X(t_i)$, the optimal self-care values $O_M(t_i)$, and the scaling factors $K_M$. A processor in communication with the input device and memory calculates the future disease control parameter value $X(t_j)$. A display is connected to the processor to display the future disease control parameter value $X(t_j)$ to a patient.

In the preferred embodiment, the system further includes a recording device in communication with the processor for recording an actual control parameter value $A(t_i)$ at time $t_i$, an actual control parameter value $A(t_j)$ at time $t_j$, and actual self-care parameters having actual self-care values $C_M(t_i)$ at time $t_i$. The processor adjusts the scaling factors $K_M$ based on the difference between the actual control parameter value $A(t_j)$ and the optimal control parameter value $R(t_j)$, the difference between the actual control parameter value $A(t_i)$ and the optimal control parameter value $R(t_i)$, and the difference between the actual self-care values $C_M(t_i)$ and the optimal self-care values $O_M(t_i)$. Thus, the scaling factors $K_M$ are customized to an individual patient to predict the effect on the disease control parameter of self-care actions performed by the individual patient.

BRIEF DESCRIPTION OF THE DRAWINGS

FIG. 2 is a sample physiological parameter entry screen according to the invention.
FIG. 3 is a sample self-care parameter entry screen according to the invention.
FIG. 10 is a schematic illustration of the entry of actual parameter values in a recording device of the system of FIG. 1.
FIG. 11 is a schematic diagram of another simulation system according to the invention.
FIG. 12 is a schematic block diagram illustrating the components of the system of FIG. 11.

DESCRIPTION

The present invention is a system and method for simulating a disease control parameter and for predicting an effect of patient self-care actions on the disease control parameter. In the following detailed description, numerous specific details are set forth in order to provide a thorough understanding of the present invention. However, it will be apparent to one of ordinary skill in the art that these specific details need not be used to practice the invention. In other instances, well known structures, interfaces, and processes are not shown in detail to avoid unnecessarily obscuring the present invention.

FIGS. 1-10 illustrate a preferred embodiment of a simulation system according to the invention. The following table illustrates a representative sampling of the types of diseases, patient self-care parameters, and disease control parameters which may be simulated using the system and method of the invention.

| Disease | Self-Care Parameters | Control Parameter |
|---|---|---|
| Diabetes | insulin, diet, exercise | blood glucose level |
| Asthma | allergens, exercise, inhaled bronchial dilators, anti-inflammatory medications | peak flow rate |
| Obesity | diet, exercise, metabolism altering medications | weight |
| Hypertension | diet, exercise, stress reduction, blood pressure medications | blood pressure |
| Coronary Artery Disease | diet, exercise, stress reduction, lipid lowering medications | cholesterol |
| Panic Disorder | stress reduction, anti-depressant medications | number of episodes |
| Nicotine Addiction | cigarettes smoked, coping behaviors | urges to smoke |

The above table is not intended as an exhaustive list, but merely as a representative sampling of the types of diseases and disease control parameters which may be simulated. For simplicity, the preferred embodiment is described with reference to a single disease, diabetes, having a single disease control parameter, a blood glucose level. However, it is to be understood that the system and method of the invention are sufficiently flexible to simulate any disease which has a measurable control parameter and which requires patient self-care actions.

Figure 1:
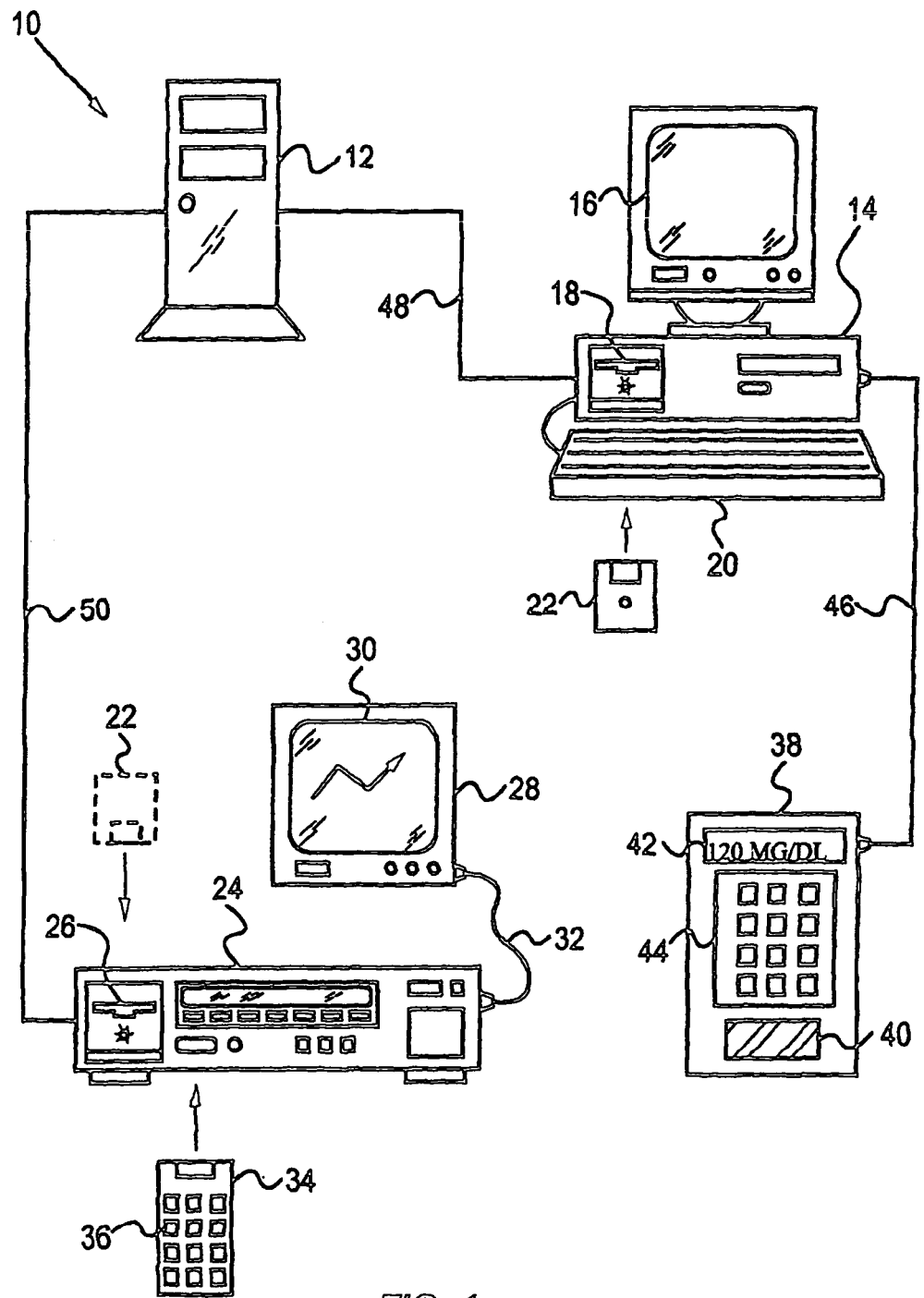
FIG. 1 is a schematic diagram of a simulation system according to the invention.

Referring to FIG. 1, a simulation system generally indicated at 10 includes a server 12 having a processor and memory for executing a simulation program which will be described in detail below. Server 12 is in communication with a healthcare provider computer 14 through a network link 48.

Healthcare provider computer 14 is preferably a personal computer located at a healthcare provider site, such as a doctor's office.

Server 12 is also in communication with a patient multi-media processor 24 through a network link 50. Patient multi-media processor 24 is located at a patient site, typically the patient's home. In the preferred embodiment, server 12 is a world wide web server, multi-media processor 24 is a web TV processor for accessing the simulation program on server 12, and links 48 and 50 are Internet links. Specific techniques for establishing client/server computer systems in this manner are well known in the art.

Healthcare provider computer 14 includes a processor and memory, a standard display 16, and a keyboard 20. Computer 14 further includes a card slot 18 for receiving a data storage card, such as a smart card 22. Computer 14 is designed to read data from card 22 and write data to card 22. Patient multi-media processor 24 includes a corresponding card slot 26 for receiving card 22. Processor 24 is designed to read data from card 22 and write data to card 22. Thus, healthcare provider computer 14 communicates with patient multi-media processor 24 via smart card 22. Such smart card data communication systems are also well known in the art.

Multi-media processor 24 is connected to a display unit 28, such as a television, by a standard connection cord 32. Display unit 28 has a screen 30 for displaying simulations to the patient. An input device 34, preferably a conventional hand-held remote control unit or keyboard, is in signal communication with processor 24. Device 34 has buttons or keys 36 for entering data in processor 24.

System 10 also includes an electronic recording device 38 for recording actual control parameter values and patient self-care data indicating actual self-care actions performed by the patient. Recording device 38 includes a measuring device 40 for producing measurements of the disease control parameter, a keypad 44 for entering the self-care data, and a display 42 for displaying the control parameter values and self-care data to the patient.

Recording device 38 is preferably portable so that the patient may carry device 38 and enter the self-care data at regular monitoring intervals. Device 38 is further connectable to healthcare provider computer 14 via a standard connection cord 46 so that the control parameter values and patient self-care data may be uploaded from device 38 to computer 14. Such recording devices for producing measurements of a disease control parameter and for recording self-care data are well known in the art. For example, U.S. Pat. No. 5,019,974 issued to Beckers on May 28, 1991 discloses such a recording device.

In the example of the preferred embodiment, the disease control parameter is the patient's blood glucose level and recording device 38 is a blood glucose meter, as shown in FIG. 10. In this embodiment, measuring device 40 is a blood glucose test strip designed to test blood received from a patient's finger 54. Device 38 is also designed to record values of the patient's diet, medications, and exercise durations entered by the patient through keypad 44. Of course, in alternative embodiments, the recording device may be a peak flow meter for recording a peak flow rate, a cholesterol meter for recording a cholesterol level, etc.

The simulation system of the present invention includes a simulation program which uses a mathematical model to calculate disease control parameter values. The following variables used in the mathematical model are defined as follows:

N=Normal time interval in which patient self-care actions are employed to make a measurable difference in the disease control parameter or a natural rhythm occurs in the disease control parameter. For diabetes and asthma, time interval N is preferably twenty-four hours. For obesity or coronary artery disease, time interval N is typically three to seven days.

$t_1, t_2, \ldots t_i, t_j \ldots t_N$=Time points at which the disease control parameter is measured by a patient. For a daily rhythm control parameter such as a blood glucose level, the time points are preferably before and after meals. For weight or cholesterol control parameters, the time points are preferably once a day or once every second day.

X(t)=Simulated disease control parameter value at time t determined by the simulation program.

R(t)=Optimal control parameter value at time t expected as a normal rhythm value of the disease control parameter at time t if the patient performs optimal self-care actions in perfect compliance from time $t_j$ to the time point immediately preceding time t.

A(t)=actual control parameter value at time t measured by the patient.

$O_M(t_i)$=Optimal self-care parameter values $O_1(t_i)$, $O_2(t_i)$, ... $O_m(t_i)$ at time $t_i$ expected to produce optimal control parameter value $R(t_j)$ at time $t_j$. For example, a diabetes patient's optimal self-care parameter values include a prescribed dose of insulin, a prescribed intake of carbohydrates, and a prescribed exercise duration.

$S_M(t_i)$=Patient self-care parameter values $S_1(t_i)$, $S_2(t_i)$, ... $S_m(t_i)$ at time $t_i$ entered in the simulation system by the patient to simulate self-care actions.

$C_M(t_i)$=Actual self-care parameter values $C_1(t_i)$, $C_2(t_i)$, ... $C_m(t_i)$ at time $t_i$ indicating actual self-care actions performed by the patient at time $t_i$.

$K_M$=Corresponding scaling factors $K_1(t_i)$, $K_2(t_i)$, ... $K_m$ for weighting the impact on a future disease control parameter value $X(t_j)$ at time $t_j$ which results from differentials between patient self-care values $S_M(t_i)$ and corresponding optimal self-care values $O_M(t_i)$.

With these definitions, future disease control parameter value $X(t_j)$ is calculated according to the equation:

$$X(t_j) = R(t_j) + (X(t_i) - R(t_i)) + \sum_M K_M(S_M(t_i) - O_M(t_i))$$

Future disease control parameter value $X(t_j)$ at time $t_j$ is determined from a prior disease control parameter value $X(t_i)$ at time $t_i$ based on an optimal control parameter value $R(t_j)$ at time $t_j$, the difference between prior disease control parameter value $X(t_i)$ and an optimal control parameter value $R(t_i)$ at time $t_i$, and a set of differentials between patient self-care values $S_M(t_i)$ and optimal self-care values $O_M(t_i)$. The differentials are multiplied by corresponding scaling factors $K_M$.

Thus, as patient self-care parameter values $S_M(t_i)$ deviate from optimal self-care parameter values $O_M(t_i)$, future disease control parameter value $x(t_j)$ deviates from optimal control parameter value $R(t_j)$ by an amount proportional to scaling factors $K_M$. This mathematical model follows the patient's own intuition and understanding that if the patient performs optimal self-care actions in perfect compliance, the patient will achieve the optimal control parameter value at the next measurement time. However, if the patient deviates from the optimal self-care actions, the disease control parameter value will deviate from the optimal value at the next measurement time.

The simulation program is also designed to generate an entry screen for entry of the patient self-care parameter values. FIG. 3 shows a sample patient self-care parameters entry screen 52 as it appears on display unit 28. The patient self-care parameters include a food exchange parameter expressed in grams of carbohydrates consumed, an insulin dose parameter expressed in units of insulin injected, and an exercise duration parameter expressed in fifteen minute units of exercise performed.

These self-care parameters are illustrative of the preferred embodiment and are not intended to limit the scope of the invention. Many different self-care parameters may be used in alternative embodiments. Screen 52 contains data fields 53 for entering a food exchange parameter value $S_1(t)$, an insulin dose parameter value $S_2(t)$, and an exercise duration parameter value $S_3(t)$. Each data field 53 has a corresponding time field 51 for entering a time point corresponding to the patient self-care parameter value. Screen 52 also includes an OK button 55 and a cancel button 57 for confirming and canceling, respectively, the values entered in screen 52.

Figures 4, 5:
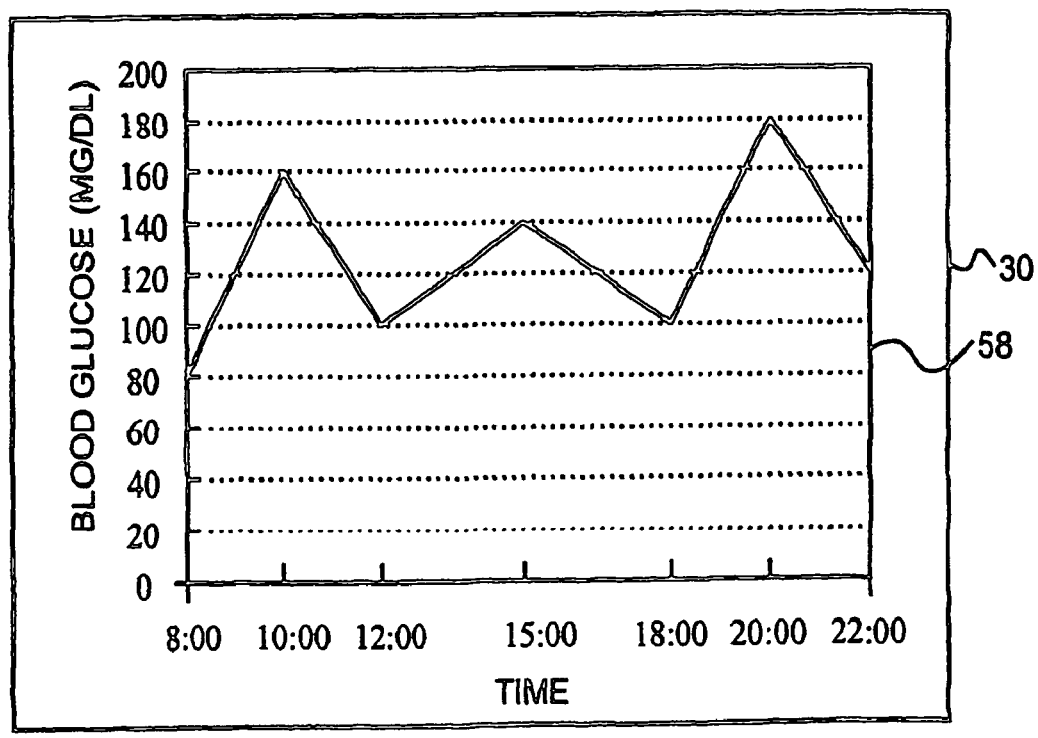
FIG. 4 is a table of values according to the invention.
FIG. 5 is a sample graph of disease control parameter values created from the table of FIG. 4.

FIG. 4 shows a sample table of values 56 created by the simulation program using the data entered by the patient through the self-care parameters entry screen. Table 56 includes a column of simulated disease control parameter values calculated by the simulation program, as will be explained in the operation section below. The simulation program is further designed to generate graphs of simulated disease control parameter values. FIG. 5 illustrates a sample graph 58 generated from table 56 as it appears on screen 30 of the display unit. Specific techniques for writing a simulation program to produce such a graph are well known in the art.

In the preferred embodiment, healthcare provider computer 14 is programmed to determine scaling factors $K_M$ from values of physiological parameters of the patient. FIG. 2 shows a sample physiological parameter entry screen 41 as it appears on the healthcare provider computer. The physiological parameters of the patient include a body mass, a metabolism rate, a fitness level, and hepatic and peripheral insulin sensitivities. These physiological parameters are illustrative of the preferred embodiment and are not intended to limit the scope of the invention. Many different physiological parameters may be used in alternative embodiments. Screen 41 includes data fields 43 for entering physiological parameter values, an OK button 45 for confirming the values, and a cancel button 47 for canceling the values.

Healthcare provider computer 14 stores indexes for determining the scaling factors from the physiological parameters entered. For example, FIG. 4 shows an insulin sensitivity scaling factor $K_2$ corresponding to insulin dose parameter value $S_2(t)$. Computer 14 is programmed to determine from a stored insulin index a value of scaling factor $K_2$ based on the entered values of the patient's body mass and insulin sensitivities. In this example, computer 14 determines a value of −40 for scaling factor $K_2$, indicating that for this patient, one unit of insulin is expected to lower the patient's blood glucose level by 40 mg/dL. Computer 14 is programmed to determine the remaining scaling factors in a similar manner. The specific indexes required to determine the scaling factors from values of a patient's physiological parameters are well known in the art.

In the preferred embodiment, healthcare provider computer 14 is also programmed to adjust scaling factors $K_M$ based on the difference between an actual control parameter value $A(t_j)$ measured at time $t_j$ and optimal control parameter value $R(t_j)$, the difference between an actual control parameter value $A(t_i)$ measured at time $t_i$ and optimal control parameter value $R(t_i)$, and the difference between actual self-care values $C_M(t_i)$ performed by the patient at time $t_i$ and optimal self-care values $O_M(t_i)$.

Scaling factors $K_M$ are adjusted to fit the mathematical model presented above, preferably using a least squares, chi-squares, or similar regressive fitting technique. Specific techniques for adjusting coefficients in a mathematical model are well known in the art. For example, a discussion of these techniques is found in "Numerical Recipes in C: The Art of Scientific Computing", Cambridge university Press, 1988.

Figure 13:
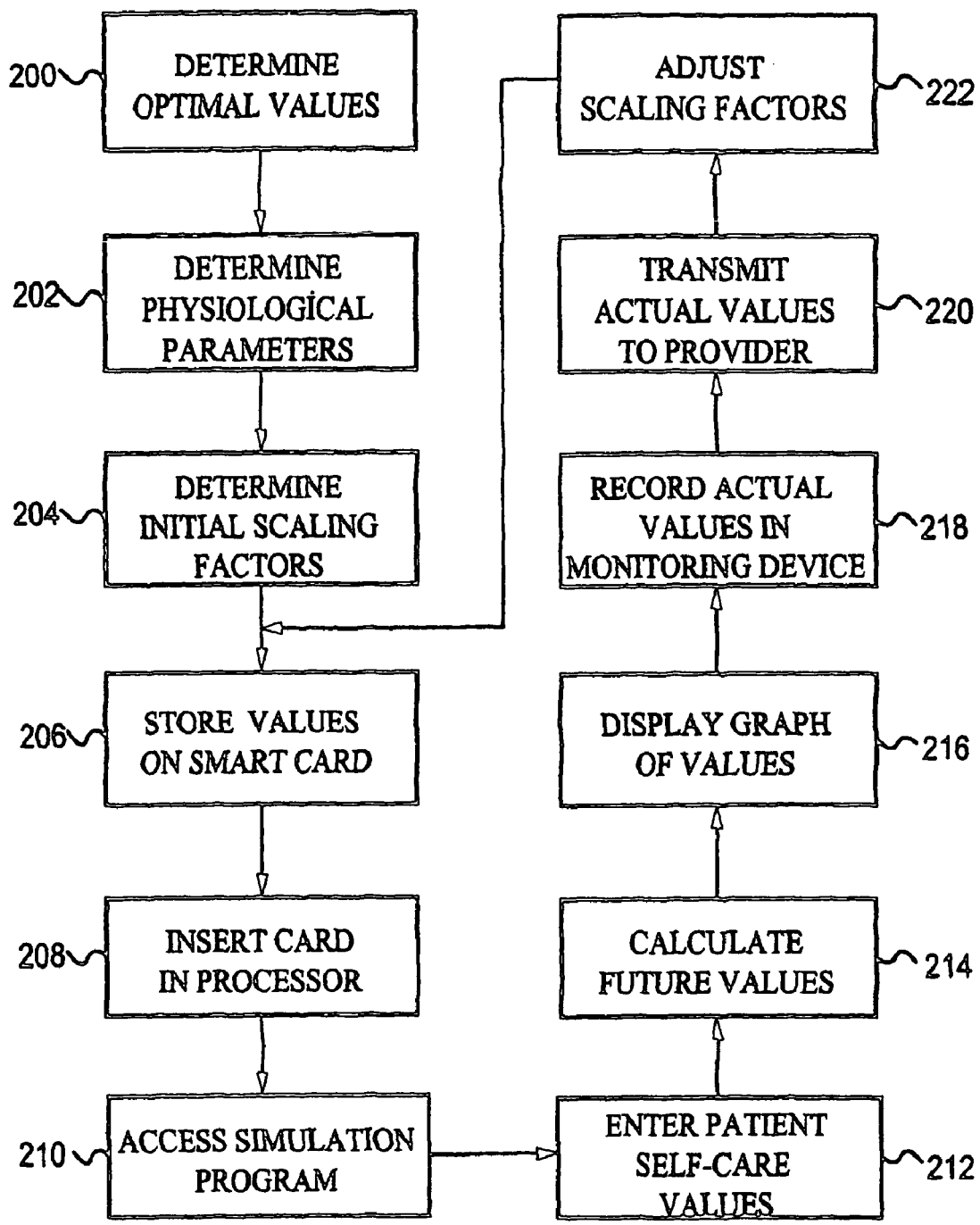
FIG. 13 is a flow chart illustrating steps included in a method of the invention.

The operation of the preferred embodiment is illustrated in FIG. 13. FIG. 13 is a flow chart illustrating a preferred method of using system 10 to simulate the disease control parameter. In step 200, optimal self-care values and optimal control parameter values for each time point are determined for the patient, preferably by the patient's healthcare provider. The optimal self-care values and optimal control parameter values are then entered and stored in provider computer 14.

In the preferred embodiment, the optimal self-care values include an optimal food exchange parameter value $O_1(t)$ expressed in grams of carbohydrates, an optimal insulin dose parameter value $O_2(t)$ expressed in units of insulin, and an optimal exercise duration parameter value $O_3(t)$ expressed in fifteen minute units of exercise. Specific techniques for prescribing optimal self-care values and optimal control parameter values for a patient are well known in the medical field.

In step 202, the healthcare provider determines the physiological parameter values of the patient and enters the physiological parameter values in computer 14 through entry screen 41. As shown in FIG. 2, the physiological parameter values include a body mass, a metabolism rate, a fitness level, and hepatic and peripheral insulin sensitivities. Specific techniques for testing a patient to determine these physiological parameter values are also well known in the medical field.

Following entry of the physiological parameter values, computer 14 determines scaling factors $K_M$ from the stored indexes, step 204. For example, FIG. 4 shows a food exchange scaling factor $K_1$ corresponding to food exchange parameter value $S_1(t)$, an insulin sensitivity scaling factor $K_2$ corresponding to insulin dose parameter value $S_2(t)$, and an exercise duration scaling factor $K_3$ corresponding to exercise duration parameter value $S_3(t)$.

In this example, computer 14 determines a value of 4 for scaling factor $K_1$, a value of −40 for scaling factor $K_2$, and a value of −5 for scaling factor $K_3$. These values indicate that one gram of carbohydrate is expected to raise the patient's blood glucose level by 4 mg/dL, one unit of insulin is expected to lower the patient's blood glucose level by 40 mg/dL, and fifteen minutes of exercise is expected to lower the patient's blood glucose level by 5 mg/dL. Of course, these values are just examples of possible scaling factors for one particular patient. The values of the scaling factors vary between patients in dependence upon the physiological parameter values determined for the patient.

The determined optimal self-care values, optimal control parameter values, and scaling factors are then stored on smart card 22, step 206. Typically, the values are stored on smart card 22 during a patient visit to the healthcare provider. The patient then takes home smart card 22 and inserts smart card 22 in patient multi-media processor 24, step 208. Next, the patient accesses the simulation program on server 12 through multi-media processor 24, step 210.

The simulation program generates self-care parameters entry screen 52, which is displayed to the patient on screen 30 of display unit 28. In step 212, the patient enters patient self-care values $S_M(t)$ and corresponding time points in data fields 53 and 51, respectively, using input device 34. The optimal self-care values, optimal control parameter values, scaling factors, and patient self-care values are transmitted from multi-media processor 24 to server 12 through link 50. In step 214, the simulation program calculates simulated disease control parameter values at each time point according to the equation:

$$X(t_j) = R(t_j) + (X(t_i) - R(t_i)) + \sum_M M(S_M(t_i) - O_M(t_i))$$

Thus, each future disease control parameter value $X(t_j)$ is calculated from optimal control parameter value $R(t_j)$, the difference between prior disease control parameter value $X(t_i)$ and optimal control parameter value $R(t_i)$, and the set of differentials between patient self-care values $S_M(t_i)$ and optimal self-care values $O_M(t_i)$. The differentials are multiplied by corresponding scaling factors $K_M$. In the preferred embodiment, first simulated disease control parameter value $X(t_1)$ at time $t_j$ is set equal to first optimal control parameter value $R(t_1)$ at time $t_1$. In an alternative embodiment, first simulated disease control parameter value $X(t_1)$ is determined from the last disease control parameter value calculated in a prior simulation.

FIGS. 4-5 illustrate a first example of simulated disease control parameter values calculated by the simulation program. Referring to FIG. 4, the simulation program creates table of values 56 having a time column, an optimal control parameter value column, a simulated control parameter value column, three self-care value differential columns indicating differentials between patient self-care parameter values and optimal self-care parameter values, and three corresponding scaling factor columns for weighting the corresponding self-care value differentials.

Table 56 illustrates the simplest simulation, in which the patient follows the optimal self-care actions in perfect compliance at each time point. In this simulation, each patient self-care parameter value equals its corresponding optimal self-care parameter value, so that the simulated disease control parameter value at each time point is simply equal to the optimal control parameter value at each time point. Referring to FIG. 5, the simulation program generates graph 58 of the simulated disease control parameter values.

Graph 58 is displayed to the patient on screen 30 of display unit 28, step 216.

Figures 6, 7:
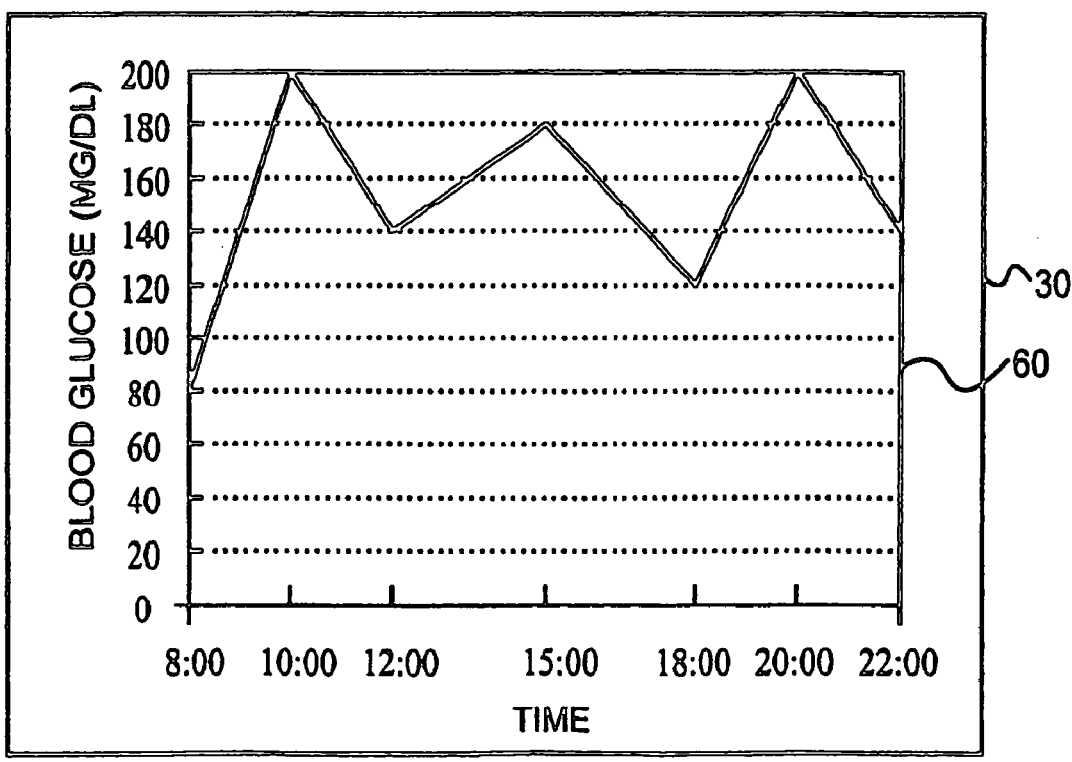
FIG. 6 is another table of values according to the invention.
FIG. 7 is a sample graph of disease control parameter values created from the table of FIG. 6.

FIGS. 6-7 illustrate a second example of simulated disease control parameter values calculated by the simulation program. FIG. 6 shows a table of values 59 having identical structure to table 56. Table 59 illustrates a simulation in which the patient consumes 10 extra grams of carbohydrates at 8:00 and exercises for 60 extra minutes at 15:00. In this simulation, the differential $S_1(t)-O_1(t)$ is equal to 10 at 8:00 due to the 10 extra grams of carbohydrates consumed by the patient. Because scaling factor $K_1$ equals 4, the simulation program calculates simulated disease control parameter value $X(t_2)$ at time point 10:00 as 40 mg/dL higher than optimal control parameter value $R(t_2)$ at 10:00.

Similarly, the differential $S_3(t)-O_3(t)$ is equal to 4 at time point 15:00 due to the 60 extra minutes of exercise performed by the patient. With simulated disease control parameter value $X(t_4)$ exceeding optimal control parameter value $R(t_4)$ by 40 mg/dL at 15:00 and with scaling factor $K_3$ equal to –5, the simulation program calculates simulated disease control parameter value $X(t_5)$ at time point 18:00 as 20 mg/dL higher than optimal control parameter value $R(t_5)$. FIG. 7 shows a graph 60 of the simulated-disease control parameter values determined in table 59. Graph 60 is displayed to the patient on screen 30 of the display unit.

Figures 8, 9:
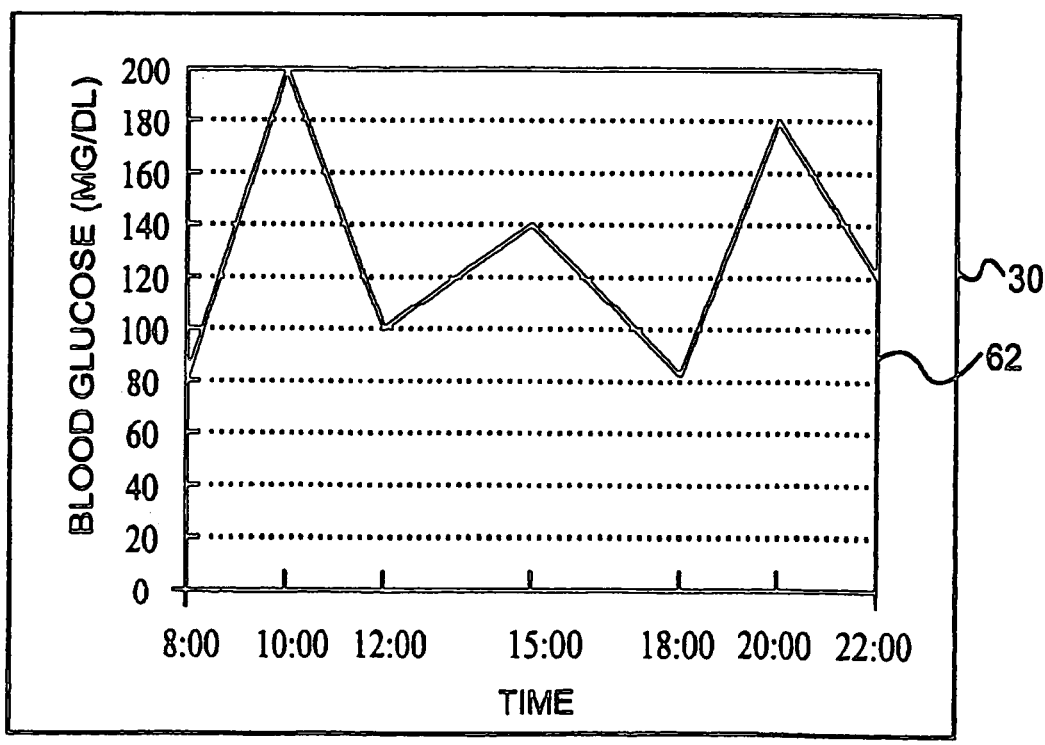
FIG. 8 is another table of values according to the invention.
FIG. 9 is a sample graph of disease control parameter values created from the table of FIG. 8.

FIGS. 8-9 illustrate a third example of simulated disease control parameter values calculated by the simulation program. Referring to FIG. 8, a table of values 61 illustrates a simulation in which the patient consumes 10 extra grams of carbohydrates at 8:00, injects 1 extra unit of insulin at 10:00, and exercises for 60 extra minutes at 15:00. The differential $S_2(t)-O_2(t)$ is equal to 1 at 10:00 due to the 1 extra unit of insulin injected by the patient. With simulated disease control parameter value $X(t_2)$ exceeding optimal control parameter value $R(t_2)$ by 40 mg/dL at 10:00, and with scaling factor $K_2$ equal to –40, the simulation program calculates simulated disease control parameter value $X(t_3)$ at time point 12:00 as equal to optimal control parameter value $R(t_3)$. FIG. 8 shows a graph 62 of the simulated disease control parameter values determined in table 61.

In addition to performing simulations with the simulation program, the patient records actual control parameter values and actual self-care values indicating actual self-care actions performed by the patient at each time point, step 218. These values are preferably recorded in recording device 38. Upon the patient's next visit to the healthcare provider, the actual control parameter values and actual self-care values are uploaded to provider computer 14, step 220. Those skilled in the art will appreciate that recording device 38 may also be networked to provider computer 14 through a modem and telephone lines or similar network connection. In this alternative embodiment, the actual control parameter values and actual self-care values are transmitted directly from the patient's home to provider computer 14.

In step 222, provider computer 14 adjusts scaling factors $K_M$ based on the difference between the actual control parameter values and the optimal control parameter values at each time point and the difference between the actual self-care values and the optimal self-care values at each time point. Scaling factors $K_M$ are adjusted to fit them to the actual patient data recorded. In this manner, the scaling factors are customized to the individual patient to enable the patient to run customized simulations. The new values of the scaling factors are stored on smart card 22 which the patient takes home and inserts in processor 24 to run new simulations.

FIGS. 11-12 illustrate a second embodiment of the invention. The second embodiment differs from the preferred embodiment in that the components of the simulation system are contained in a single stand-alone computing device 64. The second embodiment also differs from the preferred embodiment in that the system predicts each future disease control parameter value from an actual measured disease control parameter value rather than from a prior simulated disease control parameter value.

Referring to FIG. 11, computing device 64 includes a housing 66 for holding the components of device 64. Housing 66 is sufficiently compact to enable device 64 to be hand-held and carried by a patient. Device 64 also includes measuring device 40 for producing measurements of actual control parameters values and a display 70 for displaying data to the patient. Device 64 further includes a keypad 68 for entering in device 64 the optimal control parameter values, the optimal self-care values, the patient self-care parameter values, the actual self-care parameter values, and the patient's physiological parameter values.

FIG. 12 shows a schematic block diagram of the components of device 64 and their interconnections. Device 64 has a microprocessor 72 and a memory 74 operably connected to microprocessor 72. Measuring device 40 and display 70 are also connected to microprocessor 72. Keypad 68 is connected to microprocessor 72 through a standard keypad decoder 78. Microprocessor 72 is connected to an input/output port 76 for entering in device 64 a simulation program to be executed by microprocessor 72 which will be explained in detail below.

Memory 74 stores the optimal control parameter values, the optimal self-care values, the patient self-care parameter values, the actual self-care parameter values $C_M(t)$, the scaling factors, and the patient's physiological parameter values. Memory 74 also stores the simulation program to be executed by microprocessor 72 and the indexes for calculating the scaling factors from the patient's physiological parameter values.

In the second embodiment, microprocessor 72 is programmed to perform the functions performed by the healthcare provider computer of the preferred embodiment. The functions include determining scaling factors $K_M$ from the patient's physiological parameter values. The functions also include adjusting scaling factors $K_M$ based on the difference between actual control parameter value $A(t_j)$ and optimal control parameter value $R(t_j)$, the difference between actual control parameter value $A(t_i)$ and optimal control parameter value $R(t_i)$, and the difference between actual self-care values $C_M(t_i)$ and optimal self-care values $O_M(t_i)$.

Figure 14:
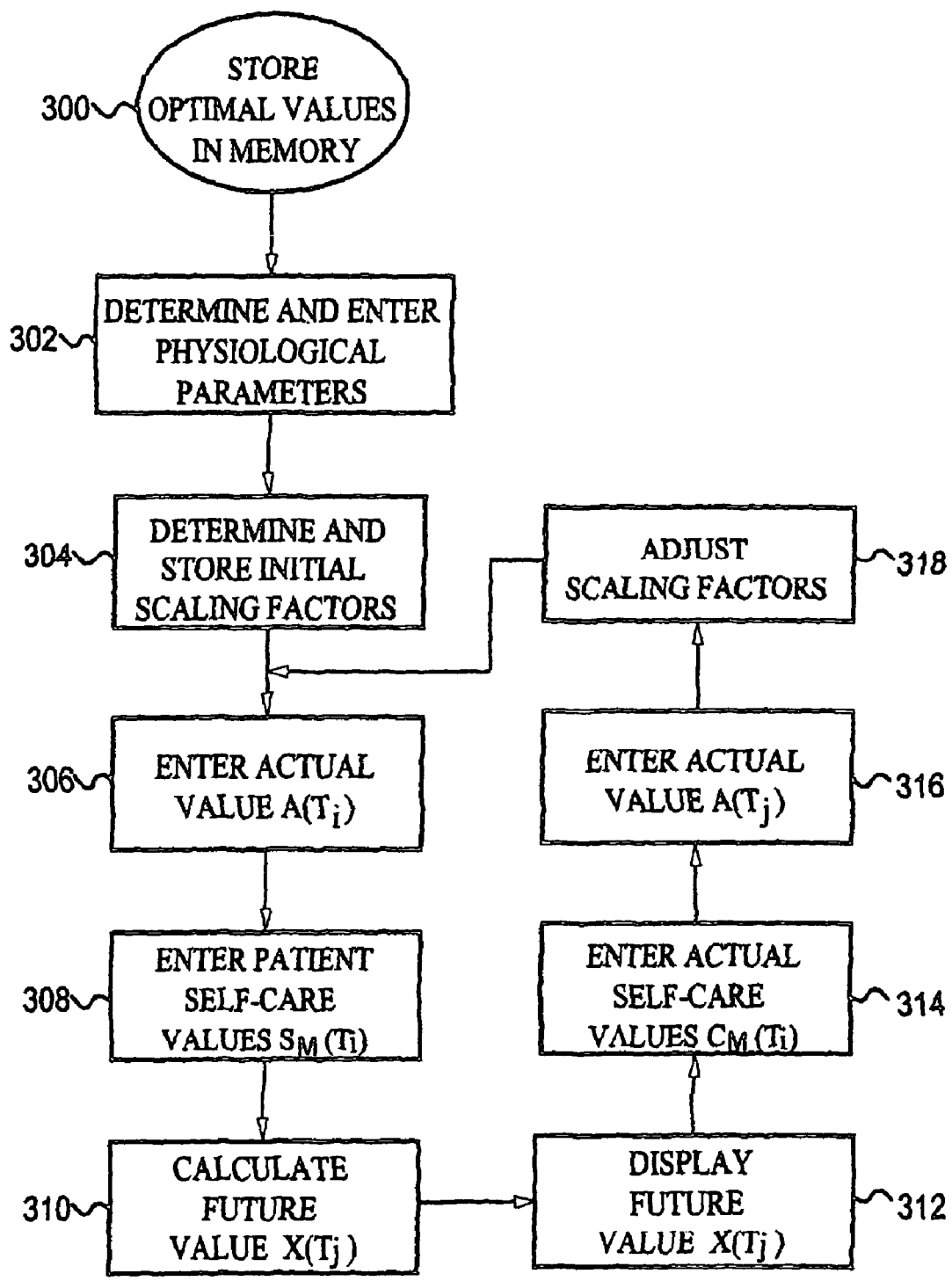
FIG. 14 is a flow chart illustrating steps included in another method of the invention.

The operation of the second embodiment is shown in FIG. 14. FIG. 14 is a flow chart illustrating a preferred method of using the system of the second embodiment to predict an effect of patient self-care actions on a disease control parameter. In step 300, the optimal control parameter values and optimal self-care values are entered in device 64 and stored in memory 74. The optimal control parameter values and optimal self-care values may be entered in device 64 either through keypad 68 or through input/output port 76.

In step 302, the patient or healthcare provider determines the patient's physiological parameter values. The physiological parameter values are then entered in device 64 through keypad 68 and stored in memory 74. Following entry of the physiological parameter values, microprocessor 72 determines scaling factors $K_M$ from the indexes stored in memory 74, step 304. Scaling factors $K_M$ are then stored in memory 74. In an alternative method of determining and storing scaling factors $K_M$ in memory 74, scaling factors $K_M$ are determined in a healthcare provider computer, as previously described in the preferred embodiment. Scaling factors $K_M$ are then entered in device 64 through keypad 68 or port 76 and stored in memory 74.

In step 306, the patient enters in microprocessor 72 actual disease control parameter $A(t_i)$. To enter actual disease control parameter $A(t_i)$, the patient places his or her finger on measurement device 40 at time $t_i$. Measurement device 40 produces a measurement of actual disease control parameter $A(ti)$ which is stored in memory 74. In step 308, the patient enters in microprocessor 72 patient self-care values $S_M(t_i)$ using keypad 68. In step 310, microprocessor 72 executes the simulation program stored in memory 74 to calculate future disease control parameter value $X(t_j)$.

The simulation program of the second embodiment differs from the simulation program of the preferred embodiment in that future disease control parameter value $X(t_j)$ is calculated from actual disease control parameter $A(t_i)$ rather than from a prior simulated disease control parameter value. In the second embodiment, future disease control parameter value $X(t_j)$ is calculated according to the equation:

$$X(t_j) = R(t_j) + (A(t_i) - R(t_i) + \sum_M K_M(S_M(t_i) - O_M(t_i))$$

Thus, future disease control parameter value $X(t_j)$ is determined from optimal control parameter value $R(t_j)$, the difference between actual disease control parameter $A(t_i)$ and optimal control parameter value $R(t_i)$, and the set of differentials between patient self-care values $S_M(t_i)$ and optimal self-care values $O_M(t_i)$. The differentials are multiplied by corresponding scaling factors $K_M$. Future disease control parameter value $X(t_j)$ is displayed to the patient on display 70, step 312.

Once future disease control parameter value $X(t_j)$ is displayed to the patient, the patient uses the value to select appropriate actual self-care actions to perform at time ti. Alternatively, the patient may perform several more simulations of future disease control parameter value $X(t_j)$ to decide appropriate self-care actions to perform at time $t_i$. Once the patient has performed the self-care actions, the patient enters in microprocessor 72 actual self-care values $C_M(t_i)$ indicating the self-care actions performed, step 314. The actual self-care values are then stored in memory 74.

The patient also enters in microprocessor 72 actual disease control parameter $A(t_j)$ measured at time $t_j$. To enter actual disease control parameter $A(t_j)$, the patient places his or her finger on measurement device 40 at time $t_j$. Measurement device 40 produces a measurement of actual disease control parameter $A(t_j)$ which is stored in memory 74, step 316. In step 318, microprocessor 72 adjusts scaling factors $K_M$ based on the difference between actual control parameter value $A(t_j)$ and optimal control parameter value $R(t_j)$, the difference between actual control parameter value $A(t_i)$ and optimal control parameter value $R(t_i)$, and the difference between actual self-care values $C_M(t_i)$ and optimal self-care values $O_M(t_i)$. In this manner, the scaling factors are customized to the individual patient to enable the patient to run customized simulations. The new values of the scaling factors are stored in memory 74 and used by microprocessor 72 in subsequent simulations.

SUMMARY, RAMIFICATIONS, AND SCOPE

Although the above description contains many specificities, these should not be construed as limitations on the scope of the invention but merely as illustrations of some of the presently preferred embodiments. Many other embodiments of the invention are possible. For example, the preferred embodiment is described in relation to diabetes. However, the system and method of the invention may be used for simulating any disease which has a measurable control parameter and which requires patient self-care actions. Similarly, the self-care parameters, corresponding scaling factors, and physiological parameters described are exemplary of just one possible embodiment. Many different self-care parameters, scaling factors, and physiological parameters may be used in alternative embodiments.

The preferred embodiment also presents a simulation system that includes a server, a healthcare provider computer, and patient multi-media processor communicating with the provider computer via a smart card. This configuration of system components is presently preferred for ease of setting, storing, and adjusting the model parameters and scaling factors under the supervision of a healthcare provider. However, those skilled in the art will recognize that many other system configurations are possible. For example, in one alternative embodiment, the system is configured as a single stand-alone computing device for executing simulations.

In another embodiment, the smart card is eliminated from the simulation system. In this embodiment, the model parameter values and scaling factors are transmitted directly to the server from the healthcare provider computer. In a further embodiment, the provider computer is also eliminated and the recording device is networked directly to the server. In this embodiment, the server is programmed to set, store, and adjust the model parameters and scaling factors based on patient data received through the recording device and patient multi-media processor.

In yet another embodiment, the server is eliminated and the simulation program is run on the patient multi-media processor. In this embodiment, the recording device and multi-media processor may also be networked directly to the provider computer, eliminating the need for a smart card. Specific techniques for networking computers and recording devices in these alternative system configurations are well known in the art.

Further, the first embodiment is described as a system for simulating a disease control parameter from simulated data and the second embodiment is described as a system for predicting a future value of a disease control parameter from actual patient data. These systems are presented in separate embodiments for clarity of illustration and ease of understanding. However, it is anticipated that both embodiments could be combined into a single simulation system for simulating disease control parameter values from simulated data, actual-patient data, or a combination of simulated and actual data.

Therefore, the scope of the invention should be determined not by the examples given but by the appended claims and their legal equivalents.

The invention claimed is:

1. A medical device for diabetes management, comprising:
a memory configured to store (i) a plurality of optimal blood glucose values at a plurality of times, (ii) a plurality of self-care values of a patient at said times, (iii) a plurality of measured blood glucose values at said times, and (iv) a plurality of optimal self-care values at said times;
a microprocessor, in communication with said memory, said microprocessor programmed to (A) generate a plurality of scaling factors customized to said patient in response to changes in any one of said self-care values or said measured blood glucose values at any one of said times and (B) calculate a future blood glucose value based on (i) a plurality of differentials, one of said differentials calculated as one of said scaling factors multiplied by differences between one of said self-care values and one of said optimal self-care values, (ii) a sum of said differentials plus (iii) a difference between one of said measured blood glucose values and a corresponding one of said optimal blood glucose values; and
a display configured to display said future blood glucose value.

2. The device of claim 1, further comprising a housing, wherein said memory and said microprocessor are housed within said housing, and further comprising an output port, said output port is integral with said housing, thereby providing a hand-held, transportable device.

3. The device of claim 2, further comprising an electronic data recording device arranged within said housing.

4. The device of claim 1, wherein said microprocessor is programmed to calculate a plurality of said future blood glucose values representative of a corresponding plurality of expected blood glucose concentrations of the patient.

5. The device of claim 1, further comprising an output port coupled to said microprocessor for establishing a communication link between said device and a healthcare provider computer and for transmitting and receiving data therebetween.

6. The device of claim 5, further comprising a modem for establishing said communication link through a communication network.

7. The device of claim 5, wherein said output port comprises an input/output port for establishing said communication link through a connection cord.

8. The device of claim 1, wherein said display is configured to display said future blood glucose values in graphical form.

9. The device of claim 1, further comprising an electronic data recording device including a glucose measurement device for measuring the measured blood glucose values, and from which the measured blood glucose values are stored in the memory.

10. The device of claim 9, wherein the glucose measuring device comprises a blood glucose meter.

11. The device of claim 1, wherein said future blood glucose values vary in response to the patient selecting appropriate self care actions by modifying one or more of said self-care values.

12. The device of claim 1, further comprising an electronic data recording device configured for receiving said measured blood glucose values.

13. The device of claim 12, wherein said electronic data recording device is in communication with said microprocessor.

14. The device of claim 1, wherein said plurality of optimal blood glucose values are further based on a future one of said optimal blood glucose values, and said future blood glucose values are calculated based further upon one or more of said future optimal blood glucose values.

15. The device of claim 1, wherein said scaling factors are downloaded to said memory from a source external to said device through at least one of (i) a keypad and (ii) a port in communication with a server computer.

16. The device of claim 15, wherein said microprocessor is further configured to adjust said scaling factors in said memory based upon said measured blood glucose values and said optimal blood glucose values such that said future blood glucose value fits the corresponding measured blood glucose values.

17. The device of claim 1, further comprising a keypad configured to receive a plurality of physiological parameters of said patient.

18. The device of claim 17, wherein said microprocessor is further configured to calculate one or more values of said scaling factors based upon said physiological parameters.

19. The device of claim 1, wherein calculation of said future blood glucose value is further based on a difference between a most recent of said measured blood glucose values and a most recent of said corresponding optimal blood glucose values.

* * * * *